United States Patent [19]
Hirano et al.

[11] Patent Number: 5,985,254
[45] Date of Patent: Nov. 16, 1999

[54] HAIR TREATMENT COMPOSITION

[75] Inventors: Yuji Hirano; Naohisa Kure, both of Tokyo, Japan

[73] Assignee: KAO Corporation, Tokyo, Japan

[21] Appl. No.: 08/734,263

[22] Filed: Oct. 21, 1996

[30]     Foreign Application Priority Data

Oct. 28, 1995   [JP]   Japan ................................ 7-303785

[51] Int. Cl.$^6$ ................................ A61K 7/09; A61K 7/11
[52] U.S. Cl. ................................ 424/70.16; 424/70.11
[58] Field of Search .............................. 424/70.11, 70.16

[56]                 References Cited

U.S. PATENT DOCUMENTS

| 4,689,217 | 8/1987 | Restaino et al. | 514/847 |
| 4,690,817 | 9/1987 | Davis et al. | 514/847 |
| 5,112,886 | 5/1992 | Phalangas . | |
| 5,338,541 | 8/1994 | Matz et al. | 424/401 |

FOREIGN PATENT DOCUMENTS

| 141 269 | 5/1985 | European Pat. Off. . |
| 257 807 | 3/1988 | European Pat. Off. . |
| 2 258 832 | 8/1975 | France . |
| 2 098 226 | 11/1982 | United Kingdom . |

OTHER PUBLICATIONS

Patent Abstracts of Japan, vol.6, No. 208 (C–130) '1086!, Oct. 20, 1982 & JP 57 116006 A (Kuraray), Jul. 19, 1982, Abstract.
Patent Abstracts of Japan, vol. 10, No. 63, (C–332) '2120!, Mar. 13, 1986 & JP 60 202103 A (Kuraray), Oct. 12, 1985, Abstract.
Patent Abstracts of Japan, vol. 12, No. 242 (C–510) '3089!, Jul. 8, 1988 & JP 63 035511 A (Shiseido), Feb. 16, 1988, Abstract.
Patent Abstracts of Japan, vol. 11, No. 124 (C–416) '2571!, Apr. 17, 1987 & JP 61 261341 A (Nitto Electric) Nov. 19, 1986, Abstract.

*Primary Examiner*—Peter F. Kulkosky
*Attorney, Agent, or Firm*—Oblon, Spivak, McClelland, Maier & Neustadt, P.C.

[57]                 ABSTRACT

A hair treatment composition which can imparts an excellent set-retaining power to the hair while maintaining the natural hair texture.

The hair treatment composition contains a polymer capable of forming a polymer film having a water vapor transmission coefficient, which is determined on the basis of a water vapor transmission rate measured in accordance with "Testing Methods for Determination of Water Vapor Transmission Rate of Moisture-proof Packaging Materials" [Japanese Industrial Standard (JIS) Z0208-1976], at a temperature of 20° C. under a relative humidity of 90%, of $0.8 \times 10^{-3}$ $g \cdot m^{-1} \cdot hr^{-1}$ or below.

8 Claims, 3 Drawing Sheets

HAIR TREATMENT COMPOSITION

FIELD OF THE INVENTION

This invention relates to a hair treatment composition which aims at retaining a hair set while maintaining the natural hair texture even under rainy weather or strong wind.

BACKGROUND OF THE INVENTION

With the recent diversified hair fashion, there arises great demand for hairstyling agents with various functions. Among all, it has been strongly required that a definite hair style is retained over a long period of time under various circumstances, in particular, under a high humidity or in strong winds.

It has been a practice to add various polymers to hairstyling agents so as to impart a strong set-retaining power. Examples of the polymers commonly employed for such the purpose include the following ones:

vinylpyrrolidone/vinyl acetate copolymer (PVP/VAE 335, manufactured by ISP);

vinylpyrrolidone/dimethyl aminoethyl methacrylate copolymer (Copolymer 845, manufactured by ISP);

methyl vinyl ether/monoalkyl maleate copolymer (Gantrez ES225, manufactured by ISP); and chitosan/dl-pyrrolidonecarboxylate (Kytamer PC, manufactured by Dainichiseika Color & Chemicals Mfg. Co., Ltd.).

Each of these polymers has a high modulus of film elasticity of $1 \times 10^8$ Pa or more (20° C., relative humidity 65%).

However, when the hair is set with a hairstyling agent containing such a polymer capable of forming a highly elastic film, there arise some problems. That is, the hair becomes stiff and the hairstyle loses natural feel both in appearance and texture.

SUMMARY OF THE INVENTION

An object of the present invention is to solve the above-mentioned problems encountering in the prior art from a viewpoint different from the modulus of film elasticity of setting polymers (i.e., without forming any highly elastic film on the hair) by providing a novel hair treatment composition which can imparts an excellent set-retaining power to the hair and protects the hairstyle from rainy or windy weather, while sustaining the natural hair texture.

The present inventors have found out that the water content of the hair varies depending on the environmental humidity but the hair-set is deformed depending not merely on the environmental humidity but largely on the transmission rate of water which is determined on the difference between the water content of the hair and the environmental humidity; and that the hair-set can be efficaciously protected from deformation by regulating the transmission rate of water into the hair, thus completing the present invention.

Accordingly, the present invention provides a hair treatment composition which comprises a polymer capable of forming a polymer film having a water vapor transmission coefficient, which is determined on the basis of a water vapor transmission rate measured in accordance with "Testing Methods for Determination of the Water Vapor Transmission Rate of Moisture-proof Packaging Materials" [Japanese Industrial Standard (JIS) Z0208-1976], at a temperature of 20° C. under a relative humidity of 90%, of $0.8 \times 10^{-3}$ $g \cdot m^{-1} \cdot hr^{-1}$ or less.

According to the hair treatment composition of the present invention, a film with a low water vapor transmission rate is formed on the hair. Therefore, even when the hair is under highly humid conditions (for example, rain), the transmission rate of the water into the hair can be suppressed at a low level. On the other hand, a hair-set is deformed at a rate largely depending on the transmission rate of water into the hair. Namely, the higher transmission rate causes the more deformation. Therefore, the hair treatment composition of the present invention makes it possible to considerably prevent the hair-set from deformation.

In the hair treatment composition of the present invention, furthermore, the modulus of elasticity of the hair is not unnecessarily elevated in order to prevent the hair-set from deformation. As a result, it becomes possible to impart a natural feel to the hair-set.

BRIEF DESCRIPTION OF THE DRAWINGS

FIG. 1(*b*) illustrates the cup assembly in a glove box during measurement of the water vapor transmission rates.

FIG. 1(*c*) illustrates a plot of weight gain versus time for polymer films.

FIG. 1(*c*) illustrates a plot of weight gain versus time for polymer films.

FIG. 1(*d*) illustrates a plot of water vapor transmission rate versus the reciprocal of film thickness, whereby the water vapor transmission coefficient, $P(g \cdot m^{-1} \cdot hr^{-1})$ is determined from the slope of the line thus obtained.

FIG. 2(*b*) illustrates the length of hair wound around a glass rod for humidity exposure.

FIG. 2(*c*) illustrates the length of hair taken off of the glass rod so as to relieve the set.

FIG. 2(*d*) illustrates the length of hair after standing for 3 hours at 20° C. under a relative humidity of 98%. $L_1$ represents a distance between the tip of the hair and the fixation face.

FIG. 2(*e*) illustrates the length of hair with preliminarily measured length $L_\alpha$. $L_1$ and $L_\alpha$ are used to measure set efficiency.

Figure 1:
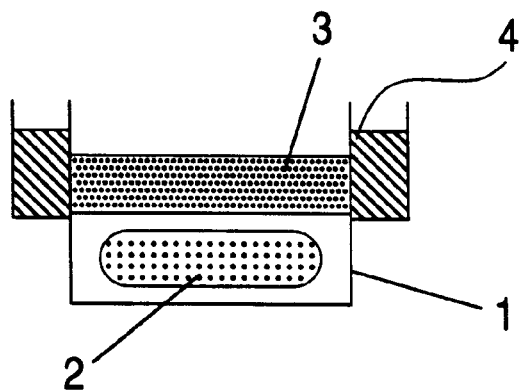
FIG. 1(*a*) illustrates a cup assembly used to measure water vapor transmission rates.
Figure 1:
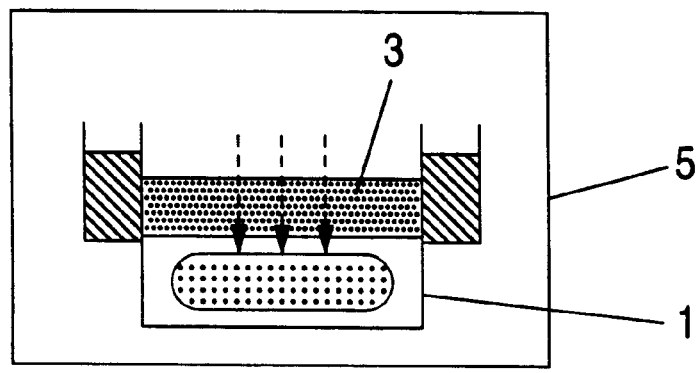
Figure 1:
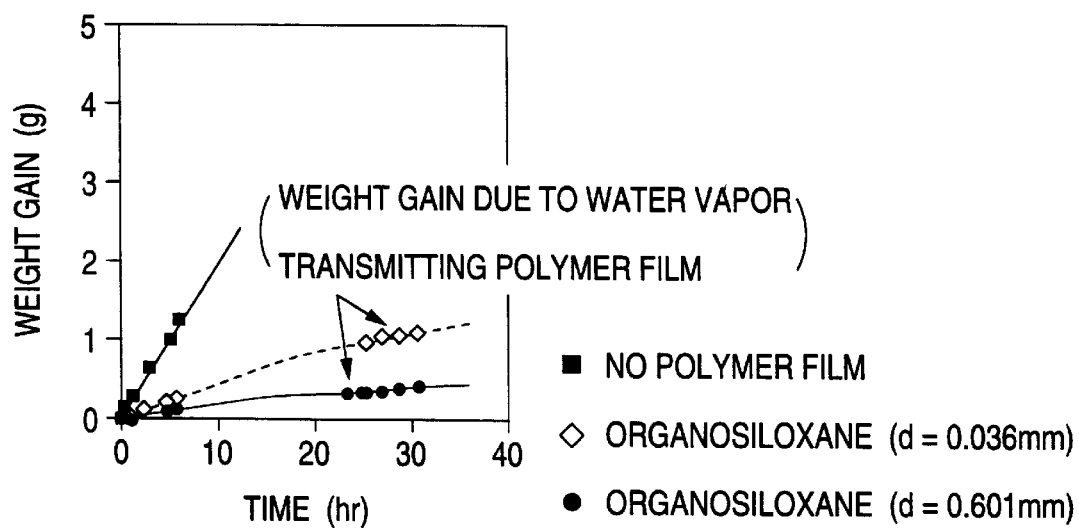
Figure 1:
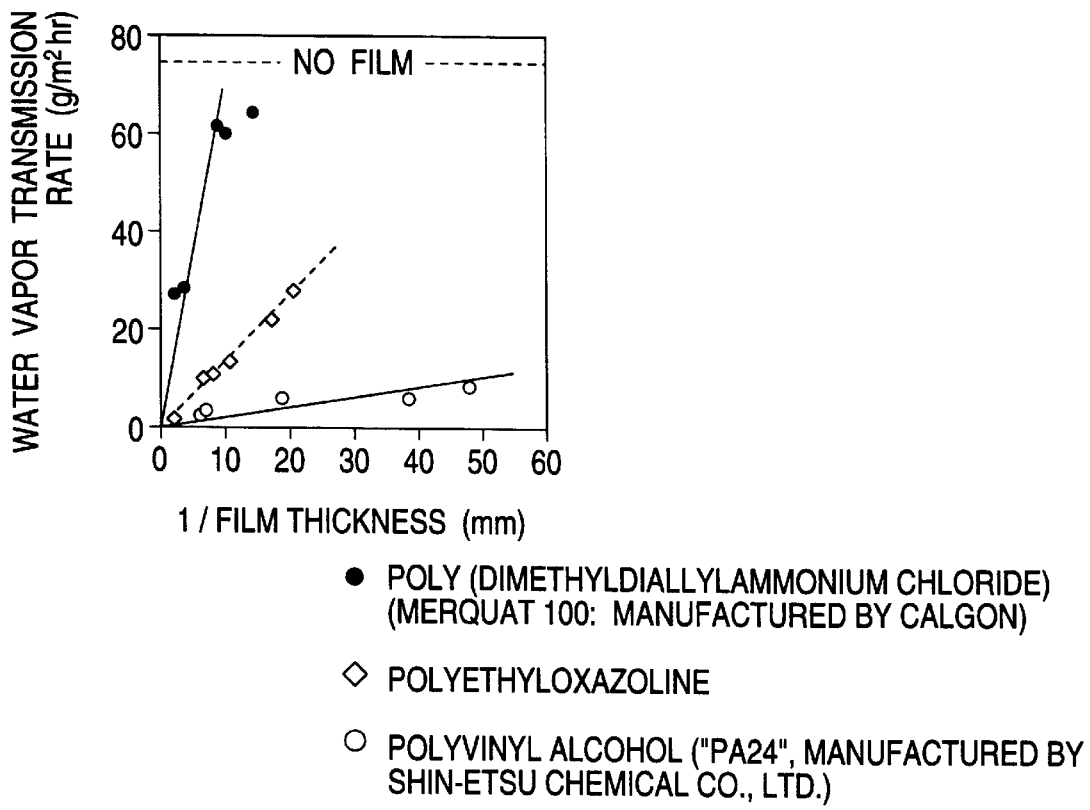

The symbols have each the following meaning.

1: Cup
2: Desiccant
3: Polymer
4: Sealing wax
5: Glove box
6: Fixation face
7: Acrylic sheet
8: Plate tress
9: Hair
10: Glass rod.

DETAILED DESCRIPTION OF THE INVENTION

Now, the embodiment mode of the present invention will be described in greater detail.

As described above, the hair treatment composition of the present invention is characterized by comprising a polymer having a water vapor transmission rate represented by a water vapor transmission coefficient of the polymer film not exceeding a definite level so as to improve the set-retaining power.

As the polymer to be contained in the hair treatment composition of the present invention for improving the set-retaining power, use is made of a polymer having a regulated water vapor transmission rate of the polymer film, namely, one having a water vapor transmission coefficient of the polymer film, which is determined on the basis of a water vapor transmission rate measured in accordance with "Testing Methods for Determination of the Water Vapor Transmission Rate of Moisture-proof Packaging Materials" [JIS-Z0208-1976], at a temperature of 20° C. under a relative humidity of 90%, of $0.8 \times 10^{-3}$ g·m$^{-1}$·hr$^{-1}$ or less, still preferably $0.6 \times 10^{-3}$ g·m$^{-1}$·hr$^{-1}$ or below.

The term "water vapor transmission rate" as used herein means the amount (g·m$^{-2}$·hr$^{-1}$) of water vapor transmission through a unit area of a polymer film within a definite time. A larger water vapor transmission rate means that water vapor can the more easily transmit through the film. However, the water vapor transmission rate varies between films depending on the film thickness, even though these film are made of the same material. Thus water vapor transmission rate cannot be employed as an indication for the comparison between the water vapor transmission rates of films differing in thickness and material from each other. In the present invention, therefore, "water vapor transmission coefficient" is used as a value showing the water vapor transmission rate of a material. "Water vapor transmission coefficient" is the slope (g·m$^{-1}$·hr$^{-1}$) of a line obtained by plotting the water vapor transmission rate against the reciprocal of the thickness. A larger water vapor transmission coefficient means that water vapor can the more easily transmit through the film.

In the present invention, the water vapor transmission coefficient of a polymer film is obtained on the basis of a water vapor transmission rate measured in accordance with "Testing Methods for Determination of the Water Vapor Transmission Rate of Moisture-proof Packaging Materials" [JIS-Z0208-1976] in the following manner. Namely, as shown in FIG. 1(a), 5 g of calcium chloride is introduced as a desiccant 2 into a cup 1 having an effective transmission sectional area of 28.27 cm$^2$. Then the cup 1 is coated with a polymer film 3 and sealed by using white bees wax pellets as a sealing wax 4. The polymer film 3 employed in this case is one formed by casting a polymer solution onto a Petri dish made of Teflon and drying under reduced pressure (i.e., a cast method) and having a thickness of from 0.1 to 0.03 mm.

As shown in FIG. 1(b), the cup coated with the polymer film 3 is allowed to stand in a glove box 5 (temperature: 20±0.1° C., humidity: 90±2%). The humidity in this glove box 5 is controlled by using an aqueous solution of a compound which is commonly used for controlling humidity (i.e., phosphoric acid, glycerol, etc.). Then the cup 1 coated with the polymer film 3 is weighed with the passage of time. After the cup 1 is allowed to stand for 20 hours so as to attain the stationary state, it is weighed at intervals of 1.5 hours.

When the cup 1 is allowed to stand in the glove box 5, namely, the weight of the cup is increased during the first several hours due to both of the water vapor transmission through the polymer film 3 and the moisture adsorbed by the polymer film 3 per se. After 20 hours, however, the weight of the cup 1 is changed exclusively by the water vapor transmission through the polymer film 3. Therefore, the cup is weighed at definite intervals (1.5 hours) after allowing to stand for 20 hours.

As shown in FIG. 1(c), the weight gain is plotted against time and the water vapor transmission rate J (g·m$^{-2}$·hr$^{-1}$) of the polymer film 3 of the corresponding thickness is determined from the slope of the line thus obtained. Next, polymer films differing in thickness from each other are also evaluated in the same manner and the water vapor transmission rate J of each polymer film is determined. As shown in FIG. 1(d), the water vapor transmission rate is plotted against the reciprocal of film thickness and thus the water vapor transmission coefficient P (g·m$^{-1}$·hr$^{-1}$) is determined from the slope of the line thus obtained.

FIG. 1(c) shows an example with the use of organosiloxane (organosiloxane A-2 described in EP-A-640643 corresponding to JP-A-7-133352; the term "JP-A" as used herein means an "unexamined published Japanese patent application") films having a thickness of 0.036 mm and 0.601 mm as the polymer film. FIG. 1(d) shows another example with the use of poly(dimethyldiallylammonium chloride) (Merquat 100: manufactured by Calgon), polyethyloxazoline (molecular weight: 50,000) and polyvinyl alcohol (PA24, manufactured by Shin-Etsu Chemical Co., Ltd.) as the polymer film.

In the present invention, use is made of a polymer capable of thus forming a polymer film with a water vapor transmission coefficient of $0.8 \times 10^{-3}$ g·m$^{-1}$·hr$^{-1}$ or less. Thus, the water vapor transmission rate of water into the hair can be sufficiently controlled in the process of the absorption of water by the hair, which makes it possible to retain the hair-set for a prolonged period of time.

Examples of the polymer capable of forming a polymer film having such the low water vapor transmission coefficient include polyolefin polymers, chlorine-containing polymers, fluorine-containing polymers, polyvinyl alcohol polymers, polyesters and polyamides. Examples of the monomers constituting vinyl polymers or copolymers include olefins such as ethylene, propylene and 1-butene, cyclic olefins such as cyclobutene, cyclopentene and cyclohexene, butadiene, styrene, acrylonitrile, vinyl alcohol, vinyl acetate, alkyl vinyl ether, vinyl chloride, vinylidene chloride, and fluorine-containing olefins such as tetrafluoroethylene, hexafluoropropylene, perfluoroalkyl vinyl ether, chlorotrifluoroethylene, butene fluoride and vinylidene fluoride.

Also, use can be made of a polymer having a polyester structure in its molecule which has been formed by polycondensation of a specific dicarboxylic acid with a diol. Examples of the dicarboxylic acid component forming such the polyester structure include terephthalic acid, isophthalic acid, o-phthalic acid, 2,6-naphthalenedicarboxylic acid, p-phenylenedicarboxylic acid, 1,4-cyclohexanedicarboxylic acid, succinic acid, adipic acid, azelaic acid, sebacic acid and sodium sulfoisophthalate. Examples of the diol component include ethylene glycol, propylene glycol, 1,4-butanediol, 1,6-hexanediol, neopentyl glycol, diethylene glycol, triethylene glycol, 1,4-cyclohexane dimethanol and bisphenol.

Further use can be made of a polymer having a polyamide structure in its molecule. Examples thereof include polymers of ε-caprolactam, ω-aminoenanthic acid, 11-aminoundecanoic acid, ω-laurolactam, ω-aminododecanoic acid, etc., hexamethylenediamine/adipic acid polycondensation product, hexamethylenediamine/sebacic acid polycondensation product, hexamethylenediamine/lauric acid polycondensation product, diaminobutane/adipic acid polycondensation product and metaxylilenediamine/adipic acid polycondensation product.

As the polymer to be used in the present invention, it is also preferable to employ one modified with an ionic group. Use of such the ionic group-modified polymer makes it possible not only to regulate the water vapor transmission coefficient of the polymer film at a low level but also to improve the adhesion of the film to the hair. In addition, flaking can be prevented and further a soft touch can be imparted to the hair thereby. In this case, the effects of the modification can be achieved even though the polymer has been modified by the ionic group only at a low ratio. On the other hand, excessive modification is not preferable, since it would cause an increase in the water vapor transmission coefficient of the polymer film. Accordingly, it is preferable that the ratio of the monomers containing the ionic group is not more than 50% by mol based on the total monomers.

Such the polymer containing an ionic group and capable of forming a polymer film with a low water vapor transmission coefficient can be obtained as a copolymer of the above-mentioned monomers with a monomer containing the ionic group. Examples of the ionic group include carboxylic acid, sulfonic acid, phosphoric acid, amine salt, quaternary ammonium salt and thiol group. Preferable examples of the monomers containing these ionic groups include acrylic acid, methacrylic acid, maleic acid, itaconic acid, styrenesulfonic acid, sodium sulfoisophthalate, methacryloylaminopropyltrimethylammonium chloride, dimethyldiallylammonium chloride, dimethylaminoethyl methacrylate diethylsulfate, imidazolinium methochloride, vinylamine and methacryloylbetaine.
Particularly, polyvinyl alcohol containing the ionic group is preferably used as the polymer.

It is preferable that the polymer to be used in the present invention is one having a degree of polymerization of at least 500. It is not preferable that the degree of polymerization is excessively low, since such the polymer is liable to be plasticized under a high humidity so as to lower the set-retaining power.

Further, it is preferable that the polymer to be used in the present invention is one capable of forming a polymer film which has a modulus of elasticity (20° C., relative humidity 65%) ranging from $0.01 \times 10^7$ Pa to $7 \times 10^7$ Pa, still preferably from $0.01 \times 10^7$ Pa to $5 \times 10^7$ Pa. It has been a practice to use a polymer having a high modulus of film elasticity in order to strengthen the set-retaining power of a hair treatment. In the present invention, however, it is riot necessary to elevate the modulus of film elasticity in order to strengthen the set-retaining power, since the set-retaining power has been improved by controlling the water vapor transmission coefficient of the film as described above. In addition, a high modulus of film elasticity makes the hair stiff and deteriorates the natural feel of the styled hair. Therefore, it is preferable in the present invention to use a polymer forming a film with a relatively low modulus of elasticity of not more than $7 \times 10^7$, still preferably, not more than $5 \times 10^7$.

When the modulus of film elasticity is excessively low, on the other hand, the polymer film is too soft for sustaining the hairstyle, even though the polymer can form a film having a very low water vapor transmission coefficient.

Accordingly, it is preferable in the present invention to use a polymer capable of forming a polymer film with a modulus of film elasticity falling within the range as defined above.

In the hair treatment composition of the present invention, use can be made of either one of the polymers capable of forming a polymer film with a low water vapor transmission coefficient or a combination of two or more of the same.

Alternatively, it is possible to use a combination of polymers which do not satisfy the above-mentioned requirements. In this case, it is preferable to blend these polymers in such a manner as to give a polymer composition satisfying the requirements of the present invention.

In the hair treatment composition of the present invention, it is preferable that the content of the polymer component is at least 0.1% by weight of the stock solution of the composition. In general, the upper limit of the content thereof is about 80% by weight.

If necessary, the hair treatment composition of the present invention may further contain various components. For example, it may contain polymers (e.g., polyethylene glycol, polymeric silicone, etc.), oils (hydrocarbon oil, ester oil, silicone oil, etc.) or fats. Further, it may contain solvents, anionic, cationic or nonionic surfactants, higher alcohols, etc. in order to solubilize or emulsify the hair treatment composition. Furthermore, it may contain various additives commonly employed in cosmetics (thickener, chelating agent, pearling agent, perfume, coloring matter, UV absorber, foaming agent, propellant, etc.), if needed.

The hair treatment composition of the present invention may be processed into various forms (hair foam, hair spray, hair set mist, hair set gel, color lotion, set lotion, blow lotion, etc.) without restriction.

EXAMPLES

To further illustrate the present invention in greater detail, the following Examples will be given.

Examples 1 to 3, Comparative Examples 1 to 4

A set lotion was prepared by mixing the components as shown in Table 1 with the use of each polymer as listed in Table 2 as the polymer components.

TABLE 1

(Composition 1)

| Component | wt. % |
| --- | --- |
| Polymer | 2 |
| Ethanol | 49 |
| Purified water | 49 |

The water vapor transmission coefficient and modulus of film elasticity (20° C., 65%) of each polymer employed were determined.

As described above, the water vapor transmission coefficient was determined by forming a film by the cast method and measuring its water vapor transmission tate in accordance with JIS-Z0208-1976 at a temperature of 20° C. under a relative humidity of 90%.

The modulus of film elasticity was determined by using the film formed by the cast method similar to the determination of the water vapor transmission coefficient as a sample (30 mm in length, 5 mm in width, 0.3 mm in thickness). The measurement was performed by using a universal tensile compression tester ("Model TCM-20S", manufactured by Shinko Tsushin Kogyo) at 20° C. under a relative humidity of 65% at a crosshead speed of 20 mm/min.

The results are shown in Table 2 below.

TABLE 2

| Ex. no. | Polymer | Water Vapor Transmission coefficient (g · m$^{-1}$ · hr$^{-1}$) | Modulus of film elasticity (Pa) |
|---|---|---|---|
| Ex. 1 | Modified polyvinyl alcohol derivative (*1) | 0.73 × 10$^{-3}$ | 0.48 × 10$^7$ |
| Ex. 2 | Modified polyvinyl alcohol derivative (*2) | 0.14 × 10$^{-3}$ | 0.34 × 10$^7$ |
| Ex. 3 | Modified polyvinyl alcohol derivative (*3) | 0.09 × 10$^{-3}$ | 3.7 × 10$^7$ |
| C. Ex. 1 | Acrylic acid/acrylate/methacrylate copolymer (*4) | 1.3 × 10$^{-3}$ | 6.3 × 10$^7$ |
| C. Ex. 2 | Vinyl methyl ether/ethyl maleate copolymer (*5) | 2.75 × 10$^{-3}$ | 44 × 10$^7$ |
| C. Ex. 3 | Acrylamide/alkyl acrylate/methacrylic acid methoxy-polyethylene glycol copolymer (*6) | 1.3 × 10$^{-3}$ | 12 × 10$^7$ |
| C. Ex. 4 | Methyl methacrylate/methacrylic acid copolymer (*7) | 0.9 × 10$^{-3}$ | 22 × 10$^7$ |

Note:
(*1): a random copolymer of vinyl alcohol/methacrylamidopropyltrimethylammonium chloride represented by the following formula (degree of modification: 10 mol %), "CGX111" manufactured by Kuraray.

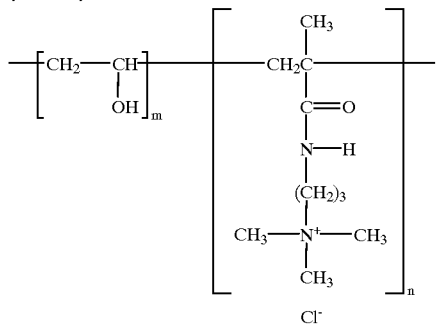

(*2): a random copolymer of vinyl alcohol/methacrylamidopropyltrimethylammonium chloride having the same structure as the above (*1) (degree of modification: 3 mol %), "CM318" manufactured by Kuraray.
(*3): a random copolymer of vinyl alcohol/itaconic acid represented by the following formula (degree of modification: 0.21 mol %), "HL12E" manufactured by Kuraray.

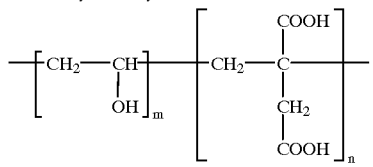

(*4): an anionic copolymer, "GK707" manufactured by Go-oh Kagaku.
(*5): an anionic copolymer, Gantrez "ES-225" manufactured by GAF Japan (neutralized with aminomethylpropanol to 10 mol % before using).
(*6): a cationic copolymer (neutralized with lactic acid to 100 mol % before using).
(*7): polymerization ratio = 50:50.

[Evaluation]

The set lotions of the above Examples and Comparative Examples were evaluated in (i) set-retaining power in moist state; (ii) flaking; and (iii) softness; each in the following manner.

(i) Set-retaining power in moist state

Figure 2:
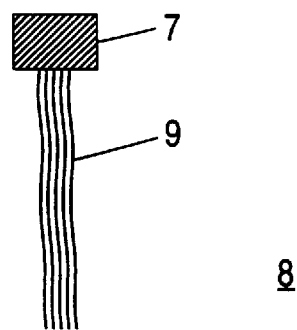
FIG. 2(*a*) illustrates a length of hair sandwiched between two acrylic plates and fixed with adhesive.
Figure 2:
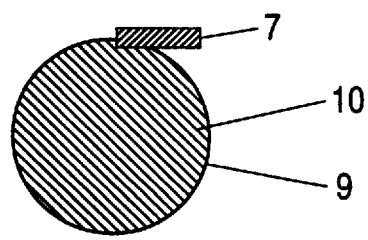
Figure 2:
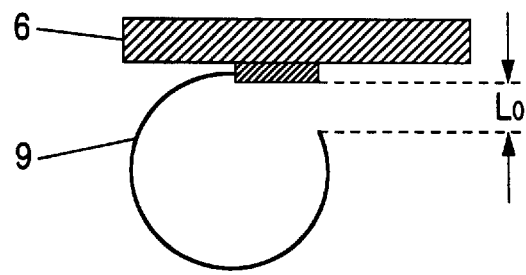
Figure 2:
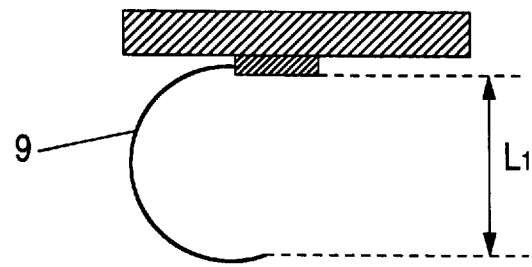
Figure 2:
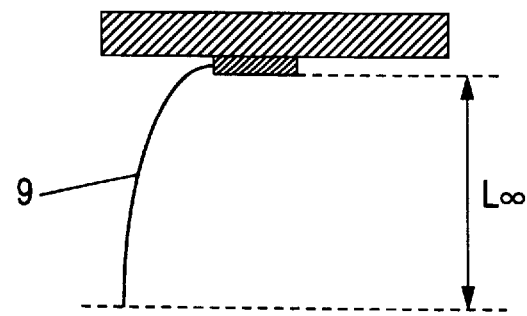

As show in FIG. 2(a), one end of hair 9 (a virgin hair bundle of a Japanese female, 10 cm in length, 1 g) was sandwiched between two acrylic plates and fixed with an adhesive, while another end was made free so as to prepare a plate tress 8. Next, the plate tress 8 was immersed in deionized water for 5 minutes and then the moisture was sufficiently eliminated with towel. Then each of the set lotions of Examples and Comparative Examples was applied onto the hair 9 of the plate tress 8 at a bathing ratio (hair:set lotion) of 1:0.2. As shown in FIG. 2(b), the hair 9 was wound around a glass rod 10 (4 cm in diameter) and allowed to stand at 20° C. under a relative humidity of 65% for 24 hours. Subsequently, the hair 9 was taken off from the glass rod 10 so as to relieve the set, as shown in FIG. 2(c). The plate tress was fixed to the fixation face 6 with the use of a double coated tape and hung. After allowing to stand at 20° C. under a relative humidity of 98% for 3 hours, the distance L1 between the tip of the hair 9 and the fixation face 6 was measured, as shown in FIG. 2(d). From this length L1 and the spontaneous length L∞ of the plate tress which had been preliminarily measured in the state shown in FIG. 2(e), the setting efficiency (%) was calculated in accordance with the following formula:

Set efficiency (%)=[(L∞−L1)/L∞]×100.

Based on the set efficiency 3 hours after relieving the set thus determined, the set-retaining power in the moist state was evaluated in 3 grades as specified below.

70% or more: Good (G).

50% to less than 70%: Fair (F).

less than 50%: Bad (B).

(ii) Flaking

A sheet tress (a virgin hair bundle of a Japans female, 10 cm in length, 1 g) was prepared in the same manner as described above. Then each of the set lotions of Examples and Comparative Examples was applied onto the hair of the plate tress at a bathing ratio (hair:set lotion) of 1:0.2. After spontaneously drying, the plate tress was combed 5 times and then flaking was evaluated with the naked eye by skilled panelists in 4 grades as specified below.

No or scarcely conspicuous flaking: Excellent (E).

Somewhat flaking but not conspicuous: Good (G).

Somewhat conspicuous flaking: Fair (F).

Conspicuous flaking: Bad (B).

(iii) Softness

A sheet tress (a virgin hair bundle of a Japans female, 10 cm in length, 1 g) was prepared in the same manner as described above. Then each of the set lotions of Examples and Comparative Examples was applied onto the hair of the plate tress at a bathing ratio (hair:set lotion) of 1:0.2. After spontaneously drying, the softness of the plate tress was evaluated by touching by skilled panelists in 4 grades as specified below.

Soft: Excellent (E).

Somewhat soft: Good (G).

Moderate: Fair (F).

Hard: Bad (B).

TABLE 3

| Ex. no. | Set-retaining power in moist state | Flaking | Softness |
|---|---|---|---|
| Ex. 1 | G | E | E |
| Ex. 2 | G | E | E |
| Ex. 3 | G | E | E |
| C. Ex. 1 | B | B | G |
| C. Ex. 2 | B | B | B |
| C. Ex. 3 | B | F | B |
| C. Ex. 4 | B | G | B |

As is apparent from the results in Table 3, the set lotions of Examples, each containing a polymer capable of forming a polymer film with a water vapor transmission coefficient of $0.8\times10^{-3}$ g·m$^{-1}$·hr$^{-1}$ or less, make it possible to achieve a good set-retaining power and to impart a soft texture.

Example 4

A hair set foam stock solution of the composition 2 as specified in Table 4 was prepared by mixing the components.

TABLE 4

(Composition 2: stock solution)

| Component | wt. % |
|---|---|
| Anionized polyvinyl alcohol ("HL12E", manufactured by Kuraray) | 3 |
| N-coconut oil fatty acid acyl-L-glutamic acid triethanolamine ("Amisoft CT12", manufactured by Ajinomoto) | 0.3 |
| Propylene glycol | 0.1 |
| α-Monoisostearyl glyceryl ether | 0.1 |
| 8-Acetyl sucrose-modified alcohol | 10.0 |
| Perfume | trace |
| Deionized water | the balance |

The stock solution thus obtained was mixed with liquefied petroleum gas employed as a propellant at a ratio of stock solution:propellant=85:15 to thereby give a hair set foam.

This hair set foam was evaluated in (i) set-retaining power in moist state; (ii) flaking; and (iii) softness; each in the same manner as described in Example 1. As a result, it showed a setting efficiency of 75%, which indicated that it had a good set-retaining power. The flaking and softness were both evaluated as E (excellent).

Example 5

A hair set spray stock solution of the composition 3 as specified in Table 5 was prepared by mixing the components.

TABLE 5

(Composition 3: stock solution)

| Component | wt. % |
|---|---|
| Anionized polyvinyl alcohol (HL12E manufactured by Kuraray) | 2 |
| α-Monoisostearyl glyceryl ether | 0.1 |
| Squalane | 0.2 |
| Propylene glycol | 0.5 |
| Deionized water | 20.0 |
| Perfume | trace |
| 8-Acetyl sucrose modified alcohol | the balance |

The stock solution thus obtained was mixed with liquefied petroleum gas employed as a propellant at a ratio of stock solution:propellant=50:50 to thereby give a hair set spray.

This hair set spray was evaluated in (i) set-retaining power in moist state; (ii) flaking; and (iii) softness; each in the same manner as described in Example 1. As a result, it showed a setting efficiency of 77%, which indicated that it had a good set-retaining power. The flaking and softness were both evaluated as E (excellent).

Example 6

A hair set gel of the composition 4 as specified in Table 6 was prepared by mixing the components.

TABLE 6

(Composition 4: stock solution)

| Component | wt. % |
|---|---|
| Anionized polyvinyl alcohol (M115 manufactured by Kuraray) [water vapor transmission coefficient: 0.11 × 10$^{-3}$ g · m$^{-1}$ · hr$^{-1}$ modulus of film elasticity: 7.0 × 10$^7$ Pa] | 0.5 |
| Anionized polyvinyl alcohol ("HL12E", manufactured by Kuraray) | 3 |
| Carboxyvinyl polymer | 1.0 |
| Triethanolamine (89%) | 1.2 |
| α-Monoisostearyl glyceryl ether | 0.1 |
| Propylene glycol | 1.0 |
| Methyl p-hydroxybenzoate | 0.2 |
| Perfume | trace |
| Deionized water | the balance |

The stock solution and the hair gel thus obtained were evaluated in (i) set-retaining power in moist state; (ii) flaking; and (iii) softness; each in the same manner as described in Example 1. As a result, it showed a setting efficiency of 80%, which indicated that it had a good set-retaining power. The flaking and softness were both evaluated as E (excellent).

According to the hair treatment composition of the present invention, an excellent set-retaining power can be imparted to the hair while maintaining the natural texture of the hair.

While the invention has been described in detail and with reference to specific embodiments thereof, it will be apparent to one skilled in the art that various changes and modification can be made therein without departing from the spirit and scope thereof.

What is claimed is:

1. A hair treatment composition, which comprises a polymer capable of forming a polymer film having a water vapor transmission coefficient, which is determined on the basis of a water vapor transmission rate measured in accordance with "Testing Methods for Determination of the Water Vapor Transmission Rate of Moisture-Proof Packaging Materials" (Japanese Industrial Standard (JIS) Z0208-1976), at a temperature of 20° C. under a relative humidity of 90%, of $0.8\times10^{-3}$ g·m$^{-1}$·hr$^{-1}$ or less, and wherein said polymer is selected from the group consisting of an ionic group-containing polyvinyl alcohol, an ionic group-containing acrylic-polyolefin and an ionic group-containing polyvinyl alcohol-polyolefin.

2. The hair treatment composition of claim 1, wherein the modulus of film elasticity of the polymer film (20° C., relative humidity 65%) ranges from $0.01\times10^7$ Pa $7\times10^7$ Pa.

3. The hair treatment composition of claim 1, wherein the ratio of a monomer containing an ionic group to the total monomers constituting the polymer is 50% by mol or below.

4. The hair treatment composition of claim 1, wherein said polymer has a degree of polymerization of at least 500.

5. The hair treatment composition of claim 1, wherein said polymer is a random copolymer of vinyl alcohol/methacrylamidopropyl trimethyl ammonium chloride (degree of modification: 10 mol %), having the following formula:

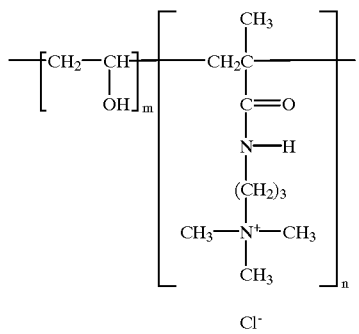

6. The hair treatment composition of claim 1, wherein said polymer is a random copolymer of vinyl alcohol/methacrylamidopropyl trimethyl ammonium chloride (degree of modification: 3 mol %) having the following formula:

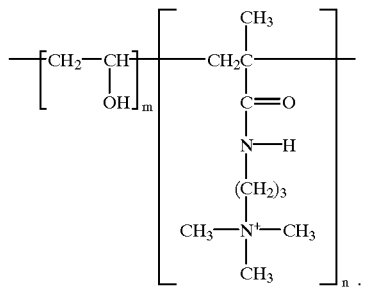

7. The hair treatment composition as claimed in claim 1, wherein said polymer is a random copolymer of vinyl alcohol/itaconic acid (degree of modification: 0.21 mol %) having the following formula:

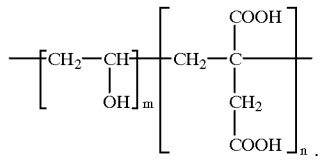

8. A method of treating hair, which comprises administering an effective amount of the hair treatment composition of claim 1 to said hair.

* * * * *